United States Patent
Ferger et al.

(10) Patent No.: US 6,752,479 B2
(45) Date of Patent: Jun. 22, 2004

(54) OBJECT STORAGE STATION AND CLIMATIC CHAMBER

(75) Inventors: Stefan Ferger, Ranstadt (DE); Hubert Heeg, Mömbris (DE); Sonja Jelinski, Hasselroth (DE)

(73) Assignee: Kendro Laboratory Products GmbH, Hanau (DE)

( * ) Notice: Subject to any disclaimer, the term of this patent is extended or adjusted under 35 U.S.C. 154(b) by 12 days.

(21) Appl. No.: 09/993,226

(22) Filed: Nov. 26, 2001

(65) Prior Publication Data

US 2002/0063077 A1 May 30, 2002

(30) Foreign Application Priority Data

Nov. 24, 2000 (DE) ......................................... 100 58 564

(51) Int. Cl.⁷ .............................................. A47B 97/00
(52) U.S. Cl. ..................................................... 312/350
(58) Field of Search ................................ 312/401, 408, 312/410, 257.1, 236, 350, 351, 334.1, 334.4

(56) References Cited

U.S. PATENT DOCUMENTS

| | | | | |
|---|---|---|---|---|
| 2,225,762 A | * | 12/1940 | Barnsteiner | ............. 312/410 X |
| 3,572,874 A | * | 3/1971 | Hassel | ......................... 312/350 |
| 3,712,698 A | * | 1/1973 | Propst et al. | ................ 312/350 |
| 4,681,381 A | * | 7/1987 | Sevey | ..................... 312/350 X |
| 5,266,272 A | | 11/1993 | Griner et al. | ................ 422/104 |
| 5,405,196 A | * | 4/1995 | Shoup et al. | ........... 312/350 X |
| 6,099,230 A | | 8/2000 | Hitch | ..................... 414/331.02 |
| 6,129,428 A | * | 10/2000 | Helwig et al. | .............. 312/114 |
| 6,273,534 B1 | * | 8/2001 | Bueley et al. | ........... 312/334.8 |
| 6,409,292 B1 | * | 6/2002 | Janowitz | .................. 312/257.1 |

FOREIGN PATENT DOCUMENTS

| WO | WO 94/04273 | | 3/1994 |
|---|---|---|---|
| WO | WO 98/05753 | * | 2/1998 |

* cited by examiner

*Primary Examiner*—James O. Hansen
(74) *Attorney, Agent, or Firm*—Baker & Hostetler LLP

(57) ABSTRACT

The invention relates to an object storage station having a front area for loading the objects, a back, and two sidewalls arranged on opposite sides, and having object holding rails with support surfaces that are arranged in pairs on opposite sides and extend substantially horizontally along the sidewalls in the interior of the object storage station. The invention is characterized in that the sidewalls have a plurality of identical, horizontally extending openings, which are arranged one above the other in the two sidewalls in identical number and position and always spaced at an identical distance from adjacent openings. The number of the openings in each sidewall corresponds to the number of the object holding rails of the sidewall and each of the openings has the same distance from the respectively closest object holding rail. The invention furthermore relates to a detachable mounting of the holding rails.

16 Claims, 4 Drawing Sheets

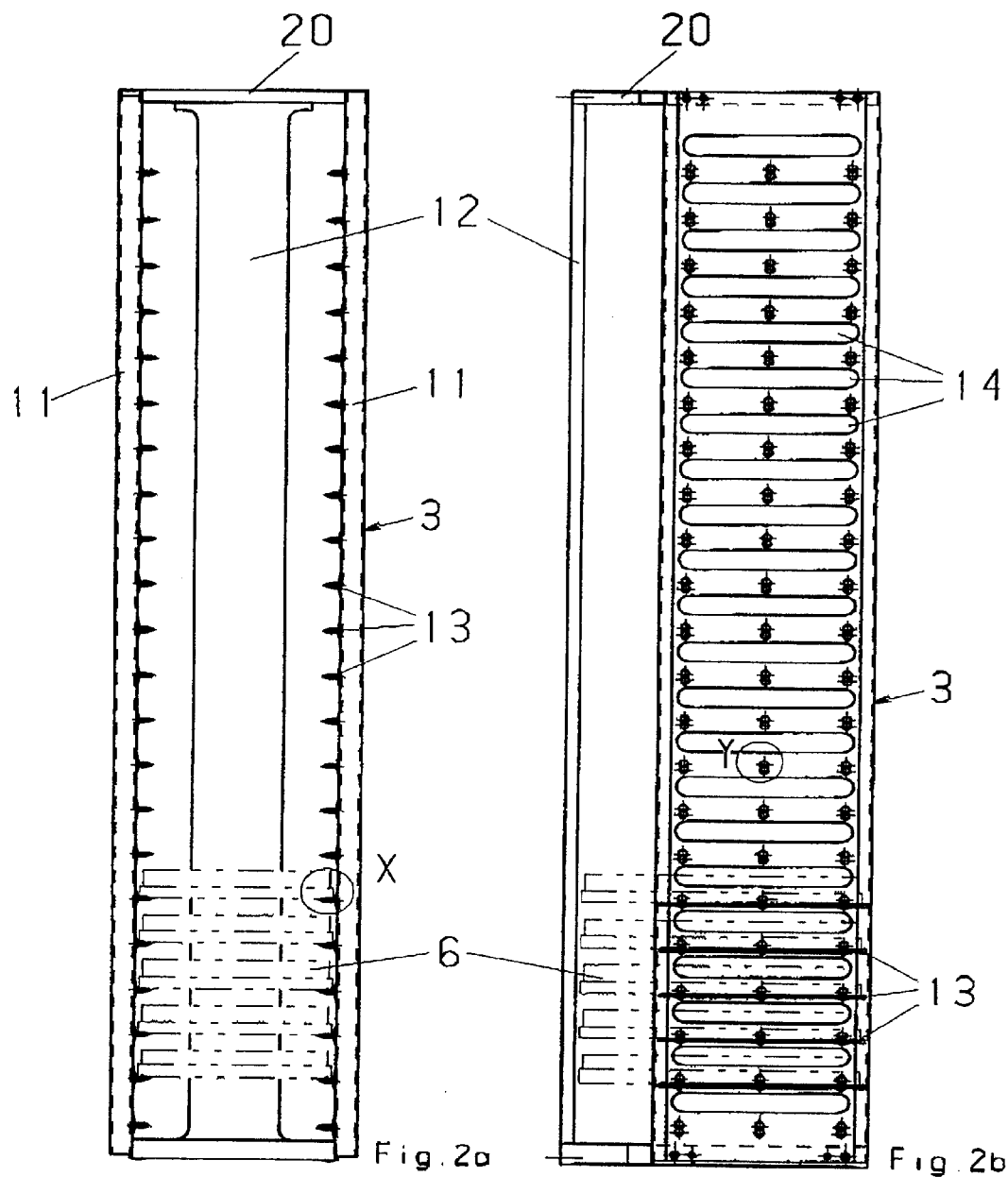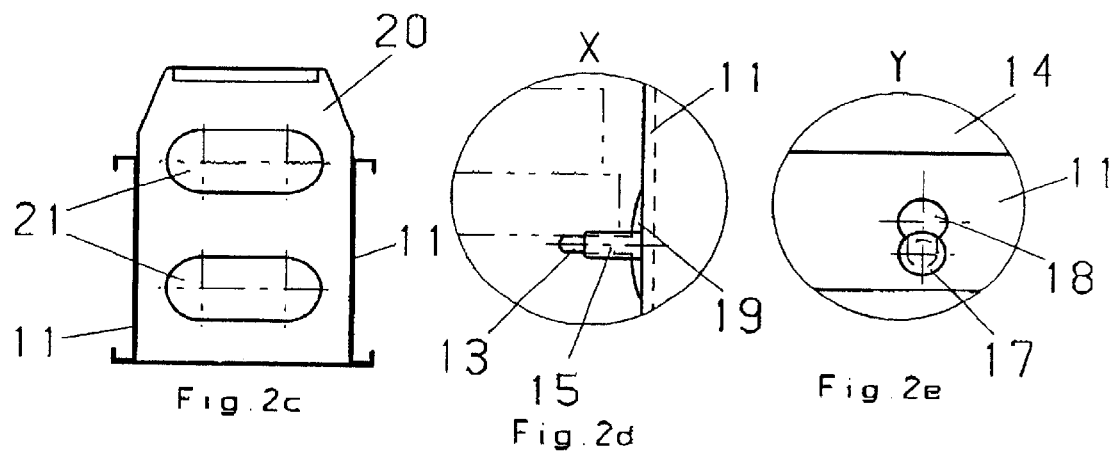

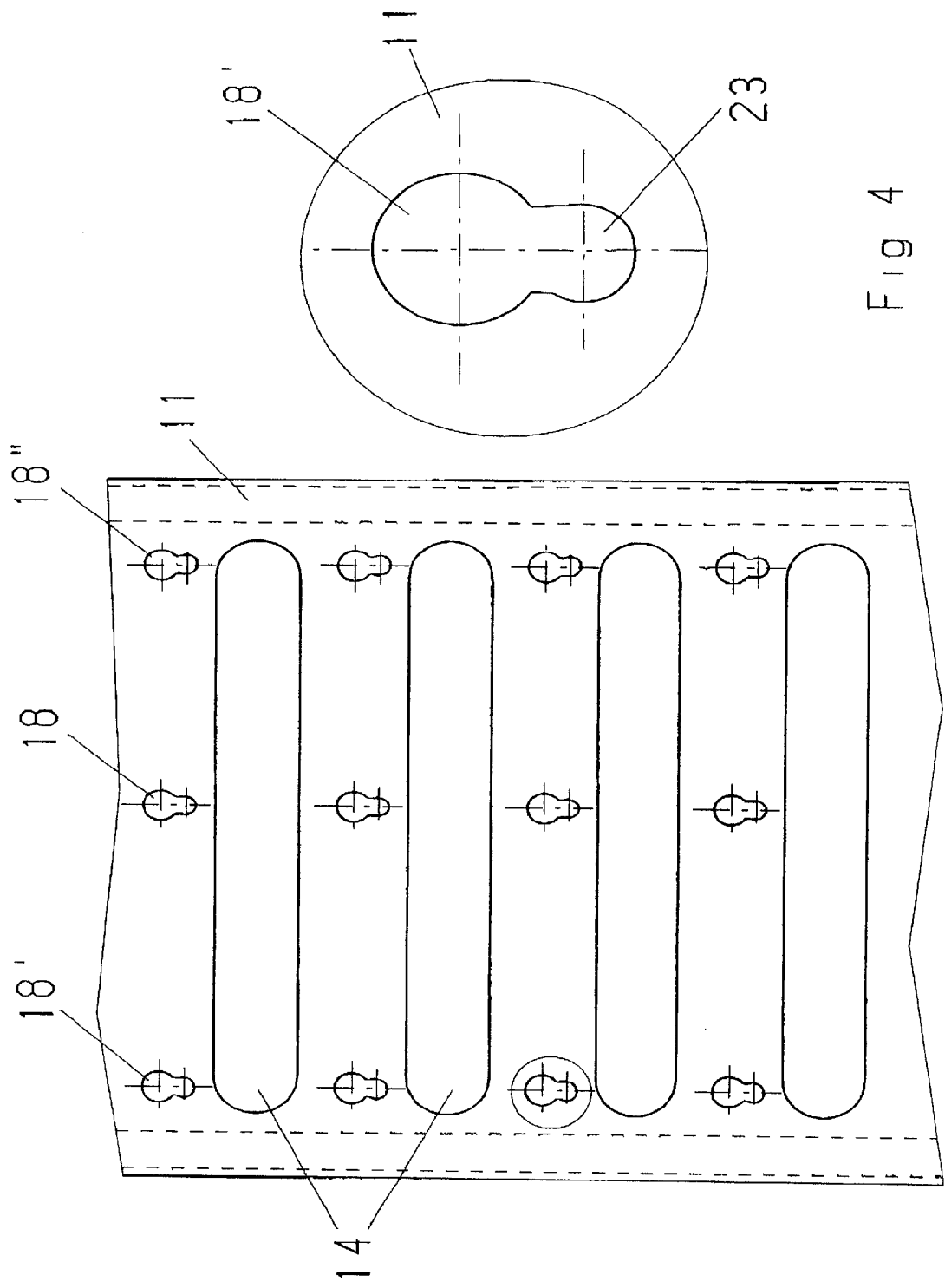

OBJECT STORAGE STATION AND CLIMATIC CHAMBER

PRIORITY

This application claims priority to foreign application 10058564.7 filed in Germany on Nov. 24, 2000 incorporated herein by reference.

FIELD OF THE INVENTION

The invention relates to an object storage station having a front area for loading the objects, a back, and two sidewalls arranged on opposite sides, and having object holding rails with support surfaces arranged in pairs on opposite sides extending substantially horizontally along the sidewalls in the interior of the object storage station. The invention further relates to a climatic chamber.

BACKGROUND OF THE INVENTION

Such object storage stations are known from WO 98/05753. The object storage stations disclosed in that document have openings along their sides. These openings are arranged differently relative to the objects to be received in the object storage stations, i.e., relative to the microtitration plates. As a result, the individual microtitration plates are subject to dissimilar airflows guided through the openings. Such dissimilar airflows lead to dissimilar growth conditions for the preparations contained in the microtitration plates. The dissimilar arrangement of the microtitration plates relative to the lateral openings leads to non-uniform contamination of the object storage station, which complicates autoclavability and reduces its success. The objects are guided in mounts that are punched out of the side parts. These mounts are point-like. They support the microtitration plates only in the front and the rear area, so that the microtitration plates have to be inserted into the object storage station precisely horizontally to prevent them from becoming jammed. The punched-out mounts, due to their design, are relatively difficult to autoclave.

SUMMARY OF THE INVENTION

The object of the present invention is to improve the known solutions and, in particular, to improve the autoclavability of the object storage stations.

According to the invention, this object is attained by the characterizing features as described herein. The sidewalls, according to the invention, have several identical, horizontally extending openings located over each other and arranged in identical number and position and always at an identical distance from adjacent openings in the two sidewalls. The number of openings in each sidewall corresponds to the number of object holding rails of that sidewall, and each opening is spaced at the same distance from the nearest object holding rail. This simplifies autoclavability since the entire area is subject to relatively uniform contamination. Such an arrangement has the further advantage that the lateral airflow flowing around the inserted objects, e.g., microtitration plates, is uniform so that the growth conditions in all the mutually superimposed microtitration plates are uniform. As a result, cell growth within the microtitration plates can be optimized.

It is particularly advantageous that the object holding rails are arranged below the openings. This protects the sides of the objects (e.g., microtitration plates) and allows the airflow to move over the objects. For simple maintenance it is particularly advantageous that the object holding rails are detachably arranged on the side parts. This is particularly advantageous if the object holding rails are made of plastic. They can also be made of metal, however, e.g., high-grade steel (as well as optionally also the other components of the object storage station) and can be fixed to the sidewalls. It is furthermore advantageous that each of the object holding rails, at least at the end facing the front area, is provided with at least one stop element on its upper side. This prevents the objects from independently sliding out of the storage station if the station is tilted, e.g., during transport. Advantageously, identical stop elements are arranged on the upper and lower sides of the object holding rails at the ends facing the front area and/or the back. This makes it possible to use standardized object holding rails in like manner on both sidewalls of the object storage station.

It is particularly advantageous that the edges of the object holding rails facing the sidewalls are provided with support strips that contact the corresponding side wall and extend at least above the support surfaces of the object holding rails. The cross section of the support strips formed perpendicularly to the sidewall and perpendicularly to the support surface of the object holding rail is wider at the junction to the object holding rails, as measured perpendicularly to the sidewall, than at the ends facing away from this junction. In this connection it is advantageous that the width of the cross section changes continuously. This creates a sloping plane on both sides of the object holding rails, so that the objects to be received are centered as they are inserted. This compensates any tolerances in width or positioning of the objects. The support strips can also extend below the object holding rails and thereby increase the stability of the object holding rails.

A second embodiment of the invention is characterized in that the object holding rails are held in at least two fixing eyelets arranged horizontally side by side in the sidewalls, by fixing projections disposed on the holding rails. The fixing eyelets extend in vertical direction. One fixing projection of a respective object holding rail is locked in the lower area of the associated fixing eyelet and the at least one additional fixing projection is held in the lower area of the associated fixing eyelet so as to be horizontally displaceable. Thus, the object holding rails are held in a defined manner but are nevertheless detachable. By locking one fixing projection while simultaneously ensuring the displaceability of additional fixing projections it is possible to compensate different temperature-dependent expansion characteristics of the sidewalls of the object storage station on the one hand and the object holding rails on the other hand. This is particularly important if the object holding rails are made of plastic whereas the sidewalls of the object storage station are normally made of metal.

Advantageously, each of the object holding rails is held to a sidewall by means of three fixing projections. Particularly advantageously, the central fixing projection is locked in the associated fixing eyelet. This ensures uniform expansion at either end of the object holding rails.

Advantageously, the fixing projections have an approximately circular cross section and between their outer end and the object holding rail a reduced cross section compared to the outer end. The upper part of a fixing eyelet is suitably shaped to receive the outer end of a fixing projection whereas the lower part is shaped to receive the reduced cross section of the fixing projection. In this case, the fixing projections of the object holding rails are guided through the larger upper end of the fixing eyelets and then pushed downwardly into the part with the reduced cross section, so that the object holding rails are securely mounted to the sidewalls. It is particularly advantageous that the cross section of the lower part of the fixing eyelets that are provided for the horizontally displaceable mounting of a fixing projection is larger than the reduced cross section of the fixing projection.

The invention furthermore relates to a climatic chamber with at least one inventive object storage station.

Advantageous embodiments of the invention are set forth in the dependent claims.

BRIEF DESCRIPTION OF THE DRAWINGS

An exemplary embodiment of the invention will now be described in greater detail with reference to the drawing in which:

FIGS. 2A–E show a front view of the object storage station (FIG. 2A), a side view (FIG. 2B), a top view (FIG. 2C), and details X (FIG. 2D) and Y (FIG. 2E)

DETAILED DESCRIPTION OF PREFERRED EMBODIMENTS OF THE INVENTION

Figure 1:
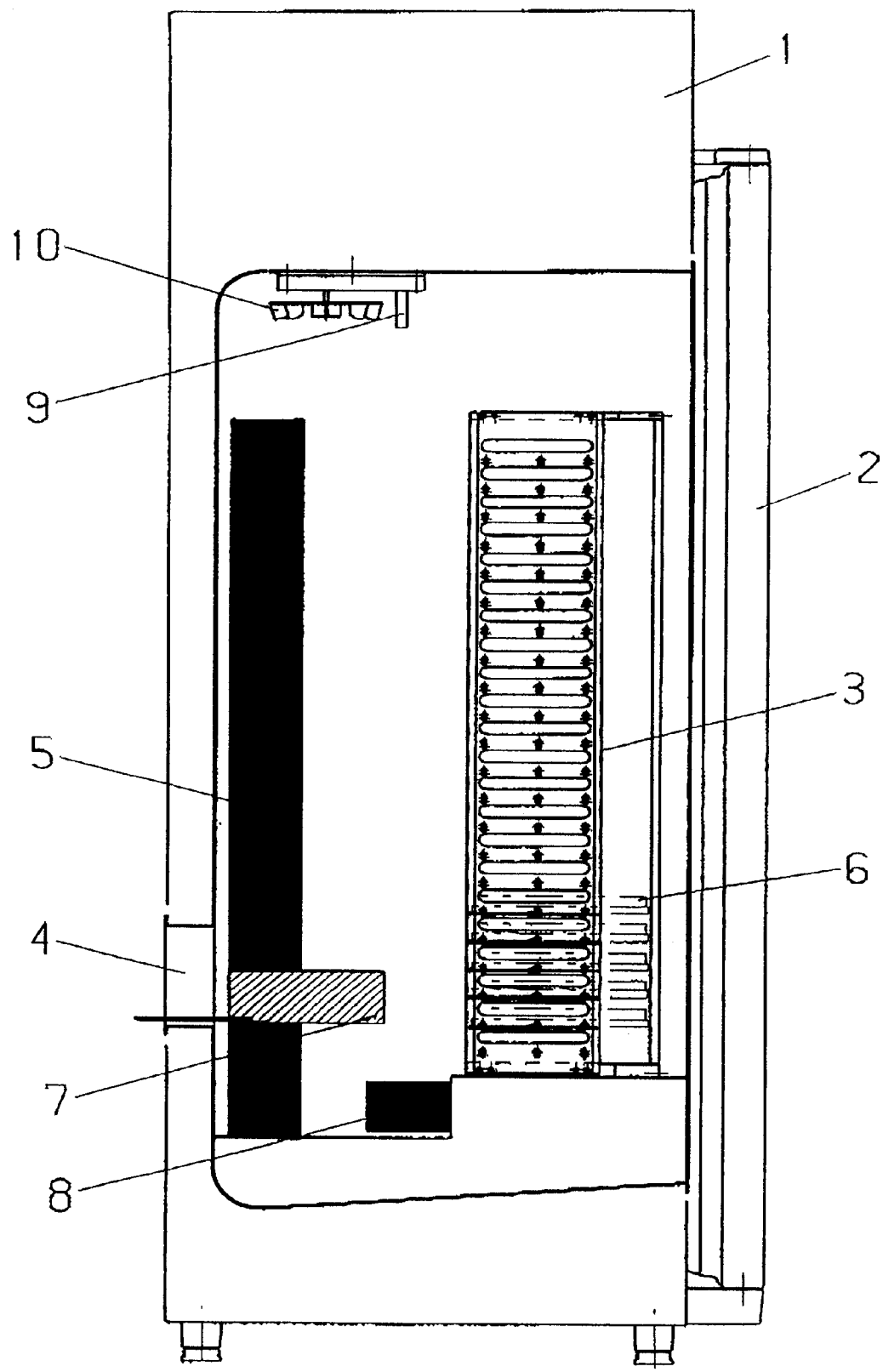
FIG. 1 is a schematic representation of a climatic chamber with an object storage station.

FIG. 1 is a side view, in partial section, of a climatic chamber 1 according to the invention. Climatic chamber 1 has a service door 2 through which the object storage stations 3 are inserted and removed and maintenance work is conducted. On the opposite side, climatic chamber 1 has a loading opening 4 through which microtitration plates 6 are inserted into and removed from the climatic chamber 1 by means of a handling system 5. The handling system 5 comprises an elevator to position the microtitration plates 6 vertically and a horizontal displacement unit 7 to position or move the microtitration plates 6 horizontally. This type of arrangement is in principle known in the prior art, for instance from WO 98/05753.

Inside the object storage station 3, a plurality of microtitration plates 6 are arranged one above the other. The object storage station 3 itself is mounted on a carrier rack 8. The upper area of the climatic chamber 1 contains a measuring cell 9 and a fan 10.

FIG. 2 shows details of an object storage station 3. FIG. 2A depicts a front view of an object storage station 3 with sidewalls 11 on opposite sides and a rear wall 12 between which microtitration plates 6 are arranged one above the other (only outlined in FIG. 2). The microtitration plates 6 are supported on object holding rails 13. Between the object holding rails 13, openings 14 are arranged one above the other in the side walls 11 (FIG. 2B). Openings 14 and object holding rails 13 are disposed in such a way that the upper edges of the microtitration plates 6 in the area of the openings 14 are disposed between the latter's upper and lower edge. The openings 14 extend the horizontal direction. The object holding rails 13 are spaced at an identical distance from the lower edge of the openings 14, respectively. At their ends, the object holding rails 13 are each provided with stop elements 15, which project upwardly and downwardly the beyond the support surface of the holding rails 13 (FIG. 2D). These stop elements prevent the microtitration plates 6 from sliding. Sliding elements 15 makes it possible to insert the object holding rails 13 interchangeably on either side of the object storage station 3. Thus, only a single configuration of the object holding rails 13 is required.

Figure 3:
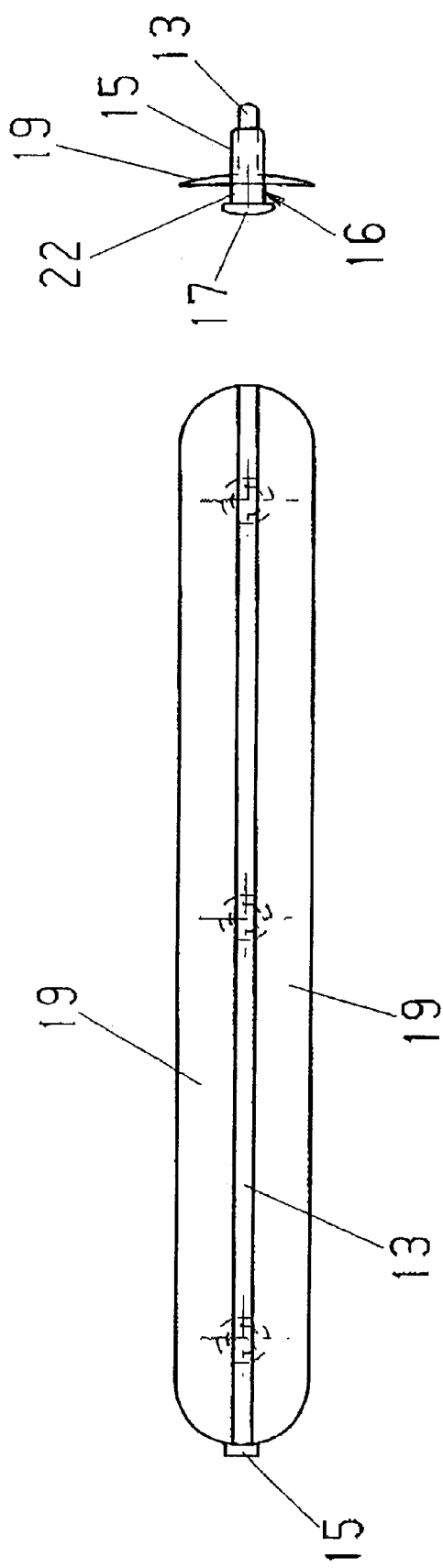
FIG. 3 shows a front view and a side view of an object holding rail, and FIG. 4 a detailed view of a sidewall of the object storage station with an enlarged view of a fixing eyelet.

FIGS. 2D and 2E illustrate the mounting of the object holding rails 13 in sidewall 11. For mounting to the sidewalls 11 the object holding rails 13 are provided with fixing projections 16 (FIG. 3), the outer ends 17 of which lie against the outwardly facing surface of sidewall 11. The fixing projections 16 are held in fixing eyelets 18. On the inside of sidewall 11, the object holding rail 13 is supported by means of support strips 19. Said support strips 19 extend above and below the object holding rail 13 and rest against sidewall 11. Their cross section increases continuously from the outer end of the support strips 19 toward the junction with the object holding rail 13. It forms a type of sloped plane on which a microtitration plate 6 that is inserted above the object holding rail 13 slides downwardly onto the object holding rail 13 and is thereby centered. The detail shows an object holding rail 13 with holding rail 13 with support strip 19 disposed therein in FIG. 3 both in a front view and a side view. The support strips 19 may be slightly bent toward their outer edges, so that their upper and lower edges lie against the side parts under tension. This spring action of the support strips ensures a firm non-rocking seat.

FIG. 2C is a top view onto an object storage station 3. The cover surface 20 is provided with handle openings 21 that serve to transport the object storage station 3. The sidewalls 11, along their front and rear end, are multiply angled to ensure high strength while keeping the material thickness as small as possible.

FIG. 4 shows a view of a sidewall 11 with details of the fixing eyelets 18, 18'; 18" disposed between the openings 14. Fixing eyelets 18 are arranged in the center between the two fixing eyelets 18' and 18" and are symmetrically configured. They have a traditional keyhole shape with an upper wider part and a lower narrower part. The cross section of he upper circular part is larger than the outer end 17 of the associate fixing projection, so that the projection can be guided through the fixing eyelet 18. The object holding rail 13 is then lowered, so that the part of the fixing projection 16 with the smaller cross section 22 is arranged in the lower, smaller part of the keyhole-shaped fixing eyelet 18. The size of the lower part is adapted to the size of the reduced cross section 22 of the fixing projection 16, so that the fixing projection is locked inside the fixing eyelet 18. To prevent any unintended lifting of the object holding rail 13, the cross section of the transition between the upper and the lower part of the keyhole can be slightly smaller than the reduced cross section 22 of the fixing projection 16, so that the latter, by pressure and due to its elasticity or the elasticity of the material of sidewall 11, can be pushed through this narrower point.

In principle, fixing eyelets 18' and 18" are configured identically to the central fixing eyelet 18. In contrast to fixing eyelet 18, however, the cross section of the lower, narrower part of the outer fixing eyelets 18', 18" is larger than the reduced cross section 22 of the fixing projection 16, so that the latter can move horizontally within the lower part 23 of fixing eyelets 18', 18". In the depicted example (FIG. 4), this enlargement is asymmetrical and is formed in outward direction pointing away from the central fixing eyelet 18. Consequently, an object holding rail 13 that expands more than the sidewall 11 when the temperature increases is freely movable in longitudinal direction and is not placed under tension.

The fixing eyelets and the fixing projections can of course be given some other suitable shape.

What is claimed is:

1. An object storage station having a front area for loading objects, a back, and two sidewalls arranged on opposite sides, and having object holding rails having edges facing the sidewalls, the object holding rails also having support surfaces arranged in pairs on opposite sides extending substantially horizontally along the sidewalls in the interior of the object storage station, characterized in that the sidewalls have a plurality of identical, horizontally extending openings arranged one above the other which are disposed in the two sidewalls in identical number and position and always at an identical distance from adjacent openings, wherein the number of the openings of each sidewall corresponds to the number of the object holding rails of the sidewall, and each opening is spaced at an identical distance from the closest object holding rail, the object storage station further characterized in that support strips are arranged along the edges of the objects holding rails facing the sidewalls, the support strips lying against a corresponding sidewall and extending at least above a support surface of the object holding rails, wherein the cross section of the support strips formed perpendicularly to the sidewall and perpendicularly to the support surface of the object holding rail is wider, as measured perpendicularly to the sidewall, at the junction to the object holding rail than at the end facing away from said junction.

2. The object storage station as claimed in claim 1, characterized in that the object holding rails are arranged below the openings.

3. The object storage station as claimed in claim 1, characterized in that the object holding rails are detachably arranged on side parts.

4. The object storage station as claimed in claim 1, characterized in that each of the object holding rails has at least one stop element located on ends of the object holding rails.

5. The object storage station as claimed in claim 4, characterized in that the at least one stop element projects upwardly and downwardly beyond the support surfaces of the object holding rails.

6. The object storage station as claimed in claim 1, characterized in that the width of the cross section of the support strips changes continuously.

7. The object storage station as claimed in claim 6, characterized in that it includes a climatic chamber.

8. An object storage station having a front area for loading the objects, a back, and two sidewalls arranged on opposite sides, and having object holding rails having edges facing the sidewalls, the object holding rails also having support surfaces arranged in pairs on opposite sides extending substantially horizontally along the sidewalls in the interior of the object storage station, characterized in that each of the object holding rails is mounted in at least two fixing eyelets, which are arranged horizontally side by side in the sidewalls, wherein the eyelets extend in a vertical direction and wherein one fixing projection of a respective object holding rail is locked within the lower area of the associated fixing eyelet and another fixing projection is held so as to be horizontally displaceable in the lower area of the associated fixing eyelet, the object storage station further characterized in that support strips are arranged along the edges of the object holding rails facing the sidewalls, the support strips lying against a corresponding sidewall and extending at least above a support surface of the object holding rails, wherein the cross section of the support strips formed perpendicularly to the sidewall and perpendicularly to the support surface of the object holding rail is wider at the junction to the object holding rail as measured perpendicularly to the sidewall than at the end facing away from the junction.

9. The object storage station as claimed in claim 8, characterized in that each of the object holding rails is mounted to a sidewall by means of three fixing projections.

10. The object storage station as claimed in claim 9, characterized in that a central fixing projection is locked in the associated fixing eyelet.

11. The object storage station as claimed in claim 8, characterized in that the fixing projections have an approximately circular cross section and between their outer ends and the object holding rail have a cross section that is reduced compared to the outer end, and wherein the upper part of the fixing eyelets has a suitable shape to receive the outer end of the fixing projection and the lower part is suitably shaped to receive the reduced cross section of the fixing projection.

12. The object storage station as claimed in claim 11, characterized in that the cross section of the lower part of the fixing eyelets is designed to hold a reduced cross section of the fixing projection.

13. The object storage station as claimed in claim 8, characterized in that the object holding rails each have at least one stop element located on ends of the object holding rails.

14. The object storage station as claimed in claim 13, characterized in that the at least one stop element projects upwardly and downwardly beyond the support surface of the object holding rails.

15. The object storage station as claimed in claim 8, characterized in that the width of the cross section changes continuously.

16. The object storage station as claimed in claim 15, characterized in that it includes a climatic chamber.

* * * * *